(12) United States Patent
Chen et al.

(10) Patent No.: US 11,969,554 B2
(45) Date of Patent: Apr. 30, 2024

(54) METHODS AND DEVICES FOR HAPTIC COMMUNICATION

(71) Applicants: The Trustees of Dartmouth College, Hanover, NH (US); FACEBOOK, INC., Menlo Park, CA (US)

(72) Inventors: Zi Chen, Hanover, NH (US); John X. J. Zhang, Hanover, NH (US); Frances Lau, San Jose, CA (US); Ali Israr, Fremont, CA (US)

(73) Assignees: THE TRUSTEES OF DARTMOUTH COLLEGE, Hanover, NH (US); FACEBOOK, INC., Menlo Park, CA (US)

(*) Notice: Subject to any disclaimer, the term of this patent is extended or adjusted under 35 U.S.C. 154(b) by 449 days.

(21) Appl. No.: 17/092,827

(22) Filed: Nov. 9, 2020

(65) Prior Publication Data
US 2021/0052845 A1   Feb. 25, 2021

Related U.S. Application Data

(63) Continuation-in-part of application No. 15/880,907, filed on Jan. 26, 2018, now Pat. No. 10,833,245.
(Continued)

(51) Int. Cl.
*H10N 30/857* (2023.01)
*A61F 2/70* (2006.01)
(Continued)

(52) U.S. Cl.
CPC ............ *A61M 21/00* (2013.01); *A61F 2/70* (2013.01); *B06B 1/0238* (2013.01);
(Continued)

(58) Field of Classification Search
CPC .......... A61M 21/00; A61M 2021/0022; A61M 2205/0294; H10N 30/857; A61F 2/70;
(Continued)

(56) References Cited

U.S. PATENT DOCUMENTS 6,867,533 B1 * 3/2005 Su .................... C08F 255/10
  310/800
2002/0158552 A1   10/2002 Nakamura et al.
(Continued)

FOREIGN PATENT DOCUMENTS

WO    WO 2016/077560 A1   5/2016

*Primary Examiner* — Jerrah Edwards
*Assistant Examiner* — Aren Patel
(74) *Attorney, Agent, or Firm* — Cozen O'Connor

(57) ABSTRACT

A haptic stimulator includes a multilayer sheet with a piezoelectric or electroactive polymer layer adapted to mechanically deform upon application of voltage, the multilayer sheet secured to a substrate, and a source of electrical stimulation coupled to drive electrodes on the polymer layer with an AC signal to vibrate the polymer layer. In particular embodiments, the polymer contains polyvinylidene fluoride, and electrodes are patterned to control local electric fields. Another haptic stimulator has first and second electrodes with an air gap and an insulating sheet between first and second electrodes, with an AC voltage driver connecting to the electrodes. In a method of providing haptic stimulation to skin an alternating current supply drives first and second electrodes, the electrodes disposed upon either a piezoelectric or electroactive polymer sheet, vibrating the polymer layer by driving the electrodes; and coupling vibrations of the polymer layer to the sensate skin.

8 Claims, 6 Drawing Sheets

Related U.S. Application Data

(60) Provisional application No. 62/450,993, filed on Jan. 26, 2017.

(51) Int. Cl.
*A61M 21/00* (2006.01)
*B06B 1/02* (2006.01)
*B06B 1/06* (2006.01)
*A61F 2/54* (2006.01)
*A61F 2/68* (2006.01)

(52) U.S. Cl.
CPC ......... *B06B 1/0688* (2013.01); *H10N 30/857* (2023.02); *A61F 2002/543* (2013.01); *A61F 2002/6827* (2013.01); *A61M 2021/0022* (2013.01); *A61M 2205/0294* (2013.01); *B06B 2201/55* (2013.01); *B06B 2201/76* (2013.01)

(58) Field of Classification Search
CPC ....... A61F 2002/543; A61F 2002/6827; B06B 1/0238; B06B 1/0688; B06B 2201/55; B06B 2201/76
See application file for complete search history.

(56) References Cited

U.S. PATENT DOCUMENTS

| | | | |
|---|---|---|---|
| 2008/0303376 A1* | 12/2008 | Jakli | H10N 30/098 428/689 |
| 2013/0009514 A1 | 1/2013 | Asaka et al. | |
| 2016/0218270 A1 | 7/2016 | Galler | |
| 2017/0196513 A1* | 7/2017 | Longinotti-Buitoni | A61B 5/7405 |
| 2018/0066636 A1* | 3/2018 | Khoshkava | C22F 1/006 |
| 2018/0081439 A1* | 3/2018 | Daniels | G06F 1/163 |
| 2018/0102717 A1* | 4/2018 | Hendriks | H10N 30/802 |
| 2018/0345117 A1* | 12/2018 | Andon | G06F 3/016 |
| 2019/0006574 A1 | 1/2019 | Mardilovich et al. | |
| 2019/0058108 A1* | 2/2019 | Guhathakurta | C08F 212/10 |

* cited by examiner

METHODS AND DEVICES FOR HAPTIC COMMUNICATION

CROSS-REFERENCE TO RELATED APPLICATIONS

The present application is a continuation-in-part of U.S. patent application Ser. No. 15/880,907 filed Jan. 26, 2018, which claims priority to U.S. Provisional Patent Application No. 62/450,993 filed 26 Jan. 2017, the entire contents of which are incorporated herein by reference.

BACKGROUND

Normal skin has sensors adapted to sense heavy and light pressure, vibration, heat, cold, and pain; collectively we call these sensations, and the ability to sense movement of zones of pressure, the sense of touch. Skin having normal sense of touch is referred to herein as sensate skin. Touch is important to normal life; in particular it allows people to grasp objects with pressure sufficient to avoid dropping the objects yet avoid crushing them. It also allows movement in the dark, alerts people to unwelcome assault by insects or infections, and allows proper positioning of fingers on keyboards without need to look at both keyboard and fingers.

Upper limb amputees wearing prosthetics often miss the sense of touch—this is why amputees given the rarely-used Kreukenberg forearm-stump-splitting procedure often reject prosthetics except for formal events where visual appearance is critical. They often find that not only is grip strength of the modified-forearm pincers strong compared to typical prosthetics, but the ability to feel with sensate skin of bare residual forearms is helpful to them.

Haptic communications is communication through these sensors of skin that provide the sense of touch.

Amputees may benefit from adding a sense of touch, or haptic communications, to prosthetic devices.

Most modern entertainment stimulates visual and auditory senses. Only a few theaters, such as "4-D" theaters at Universal Studios amusement parks in Orlando, Florida, are equipped to stimulate senses other than vision and hearing through air and scent puffers, seat-moving actuators, and water sprinklers—the sense of touch is largely unused in entertainment systems. It is expected that adding haptic communication to existing virtual-reality and other entertainment systems may enhance user experiences.

Users of remote teleoperation devices, such as handling equipment in hazardous environments, may also benefit from haptic communications.

Blind people may also benefit from artificial vision systems that present edge-enhanced images through haptic stimulation devices deployed against sensate skin of their back and shoulders.

SUMMARY

A haptic stimulator includes a multilayer sheet with a layer of smart material, for example, either a piezoelectric or electroactive material, adapted to mechanically deform upon application of a voltage to the smart material, the multilayer sheet secured to a substrate, and a source of electrical stimulation coupled to drive the electrodes on the polymer layer with an AC signal to vibrate the polymer layer. In particular embodiments, the polymer contains polyvinylidene fluoride.

In another embodiment, haptic stimulator has a first and second electrode with an air gap and an insulating sheet between first and second electrodes, with a high voltage AC driver driving the electrodes.

In a method of providing haptic stimulation to skin an alternating current signal generator drives a first and second electrode, whereby the second electrode disposed upon either a piezoelectric or electroactive polymer sheet, vibrating the polymer layer by driving the electrodes; and coupling vibrations of the polymer layer to the sensate skin.

DETAILED DESCRIPTION OF THE EMBODIMENTS

We propose vibratory haptic-stimulation devices. In embodiments, these haptic-stimulation devices are based upon polymeric piezoelectric materials. In embodiments mesoporous polyvinylidene fluoride (PVDF) and PVDF copolymers are used as piezoelectric materials in sensors and actuators for haptic communications. These PVDF devices serve both as pressure sensors for use in prosthetics, and as actuators for pressing against or vibrating against sensate skin. The sensate skin may be skin of a residual limb or of other parts of the body such as the back of chest and abdomen.

The biological mechanoreceptors in human touch sensing can detect whether a material is rough or smooth, hard or soft, sticky or slippery, and at rest or in motion. We aim to simulate human touch with a matrix of simple but scalable actuating elements, where each element is programmable for local sensing and actuation. This can assist in virtual reality, to telecommunicate social caring or conversational intentions through touch over a long distance.

The devices have two modes of operation; first, as they respond to external forces, such as pressure on a prosthetic glove over a prosthetic hand, they generate voltages that can be sensed. Second, when sufficient high alternating voltages are applied to the PVDF or PVDF-TrFE piezoelectric films, they change shape producing vibrations that can be felt by sensate skin operating as haptic skin-stimulation actuators.

In the first mode they can serve as pressure or touch sensors; these can be embedded in a surface of a prosthetic to serve as touch sensors and the electronic device can stimulate skin of a residual limb with signals derived from the pressure or touch sensors. In the second mode they can serve as actuators to stimulate touch sensors in adjacent skin, or, since the piezoelectric film electrical response varies with mechanical load on these actuators, they can also serve as pressure sensors.

An example of a PVDF copolymer is porous PVDF-TrFE (polyvinylidene fluoride-trifluoroethylene) film is presented in PCT/US15/60342, the contents of which are incorporated herein by reference.

A bistable structure is one that has a first and a second stable mechanical shape, particularly where they are stabilized by different curvature axes. Some embodiments make use of bistable or multistable structures to provide a pronounced "snap" action when used as sensors. Other embodiments make use of bistable or multistable structures and resulting "snap" action to provide sharper vibratory waveforms with greater harmonic content when used as haptic skin stimulators.

Figure 1:
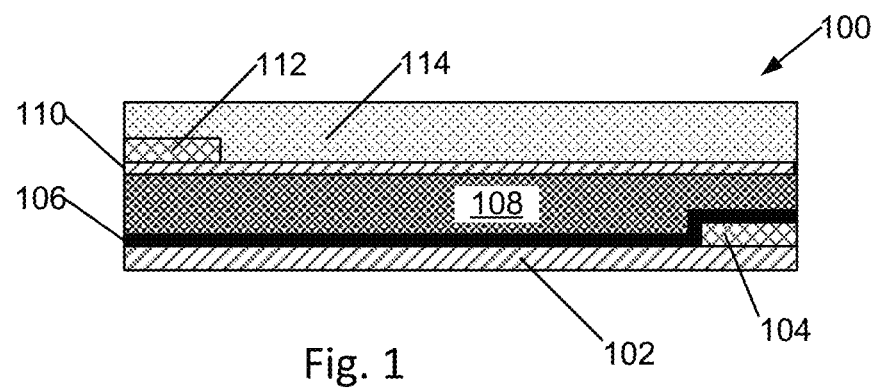
FIG. 1 is a cross sectional view of a polyvinylidene fluoride (PVDF) piezoelectric structure having electrodes on a top and bottom surface.

FIG. 1 is a cross sectional view of a dual-sided-electrodes mesoporous polyvinylidene fluoride (PVDF) multilayer piezoelectric structure 100, polyvinylidene fluoride being a polymeric piezoelectric material. A supporting layer 102 is coated and masked with electrode interconnect 104, then a bottom electrically-conductive electrode layer 106 is applied. Bottom electrically-conductive electrode layer 106 and interconnect 104 are typically metallic. A mesoporous layer of polyvinylidene difluoride (PVDF) 108 is then formed atop the conductive electrode layer 106. The PVDF film is polarized in a strong electric field to induce piezoelectricity. Atop the PVDF layer is a top electrical contact layer 110 and an interconnect layer 112. An insulating plastic layer 114 is provided atop the entire structure, in biological applications the insulating layer is formed of a biocompatible plastic. Supporting layer 102 is chosen to be a moderately stiff material such as polyimide like Kapton, or polydimethylsiloxane (PMDS), supporting layer. PVDF copolymers have much smaller Young's modulus than piezoelectric ceramics like lead ziconate titante (PZT) or solid piezoelectric crystals like quartz, and have relatively high piezoelectric constants.

In particular embodiments the top and/or bottom electrode contact layers are patterned to provide design engineers with control of electric field distributions within the piezoelectric polymer layer.

Figure 2:
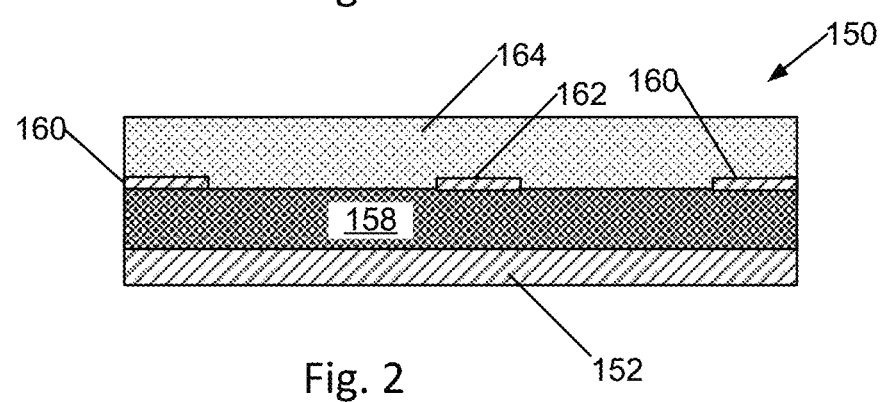
FIG. 2 is a cross sectional view of a PVDF piezoelectric structure having interdigitated electrodes.

FIG. 2 is a cross sectional view of a single-sided-electrodes PVDF multilayer piezoelectric structure 150. A supporting layer 152 is coated with a mesoporous layer of polyvinylidene difluoride (PVDF) 158. Atop the PVDF layer is a top electrode layer forming portions of first electrode 160 interdigitated with second electrode 162. In particular embodiments the electrode contact layer pattern is chosen to control electric field distributions within the piezoelectric polymer layer. An insulating plastic layer 164 is provided atop the entire structure, in biological applications the insulating layer is formed of a biocompatible plastic.

PVDF Ring-Shaped Interdigitated Transducer

Piezoelectric actuators have been developed using various piezoelectric materials and electrode patterns. Ring-shaped interdigitated electrodes are used to excite the film for electrical excitation of the film's resonance. Frequencies associated with this resonance are determined by material properties and geometric parameters, and vibration amplitude also depends on the input electric excitation magnitude and electric patterns. With our polymeric piezoelectric materials, including PVDF, frequencies in the 60 to 200 hertz range are possible.

Previous ring-shaped interdigitated transducers used piezoelectric ceramics such as PMN-PT and PZT with resonance frequencies of the base vibrational mode usually higher than 1 kHz, and vibration amplitudes at resonance typically of several micrometers. These vibrations are less efficient at stimulating skin than the frequencies in the 60 to 200 hertz range achieved with polymeric piezoelectric materials.

PVDF and PVDF copolymers, such as PVDF-TrFE (polyvinylidene fluoride-trifluoroethylene) have much smaller Young's modulus than piezoelectric ceramics, and have relatively high piezoelectric constants. Ring-shaped interdigitated transducers (IDTs) based on PVDF films excite large out-of-plane vibration amplitude at the resonance frequency due to the films' relatively low stiffness, and the resonance frequency can be reduced by orders of magnitude below resonant frequencies of similar piezoelectric transducers. Thus, PVDF ring-shaped IDTs can form actuators operating at low frequencies and with large-displacement mechanical outputs.

Figure 3:
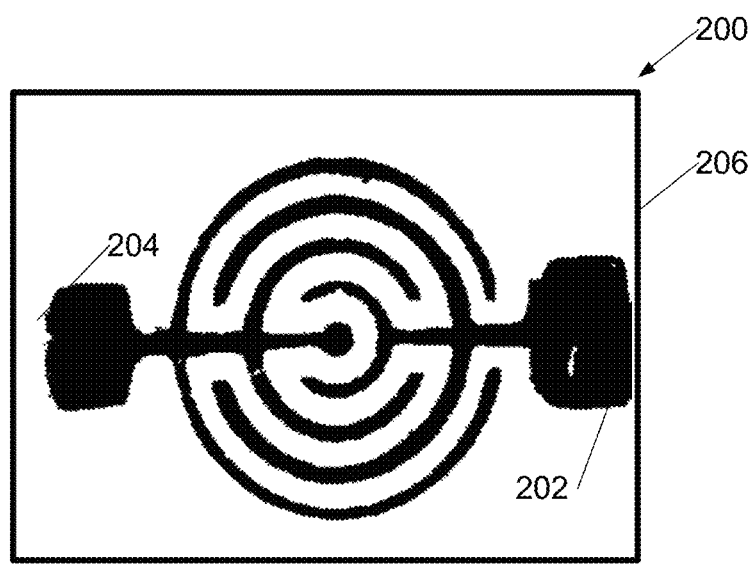
FIG. 3 is a top plan view of a PVDF piezoelectric interdigitated-electrode structure as fabricated and tested in vivo

A haptic stimulator in form of a piezoelectric device 200 (FIG. 3) with interdigitated electrodes 202, 204 is formed of the single-sided electrodes PVDF multilayer structure 150 mounted to a rectangular frame 206. Devices of this type have been fabricated and tested in sizes of 2 cm and 2.8 cm diameter, in a rectangular frame sized 3 by 4 centimeters, with resonant frequencies between 80 and 125 hertz, resonant frequency may in part be controlled by design of thickness of the PVDF film. A small air gap is provided beneath the PVDF structure. These devices produced vibrations sufficient to stimulate the biological touch sensors in human skin. The 2 cm diameter device achieved low frequency displacement of 80 microns using a PVDF film thickness of 28 microns, under load 5 millinewtons (mN) of force was achieved with 1 kv excitation voltages. The 2.8 cm diameter device achieved 30 mN of force with a 52 micron PVDF film thickness.

At frequencies of 20 and 84 hertz and 500 volt AC stimulation, the 2.8 cm device with PVDF film thickness of 52 microns and positioned on an arm of a human volunteer provided sufficient displacement for vibrations to be felt as of moderate strength, thereby functioning as a haptic stimulator.

Bimorph-Pocket Design

Bimorph is a commonly seen structure employed to generate large displacement using a thin plate. The bimorph design uses a multilayer structure 250 (FIG. 4) having a supporting layer 252, a bottom electrode 254, a lower piezoelectric layer 256, and a center electrode 258. It also has an upper piezoelectric layer 260 and top electrode 262 covered by a passivation and insulation layer 264. With thin PVDF piezoelectric layers 256, 260, the bimorph typically generates more force than the embodiment of FIG. 1, but requires a bipolar power supply.

Figure 5:
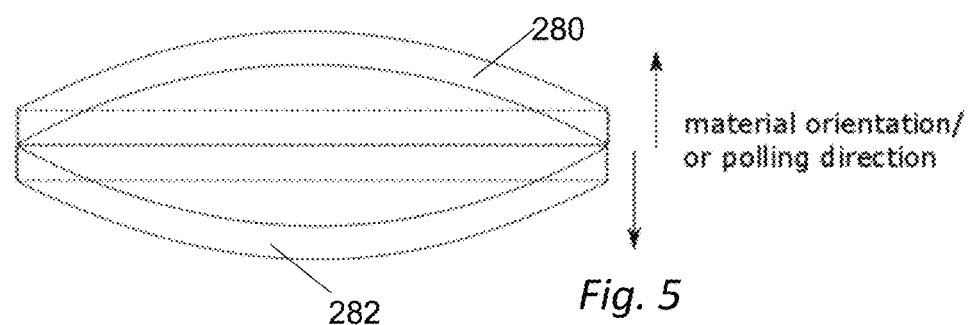
FIG. 5 is a cross section of a bimorph-pocket device.

A pocket design is formed by mounting two, back-to-back, bimorphs such that the bimorphs 280, 282 (FIG. 5) warp in opposite directions when activated by a voltage. In an alternative embodiment, multiple bimorphs are stacked. With five stacked bimorphs we expect to be able to achieve maximum forces of one newton and displacement of 2.5 mm. with 1 kv voltages, although this level of force and vibration amplitude would be downright painful if used for haptic communications. With a haptic stimulator having fewer than five stacked bimorphs and reduced voltages, vibration levels felt by a user over a range from barely perceptible to strong, but not painful, vibration can be achieved.

Prosthetic Sensory System

Figure 6:
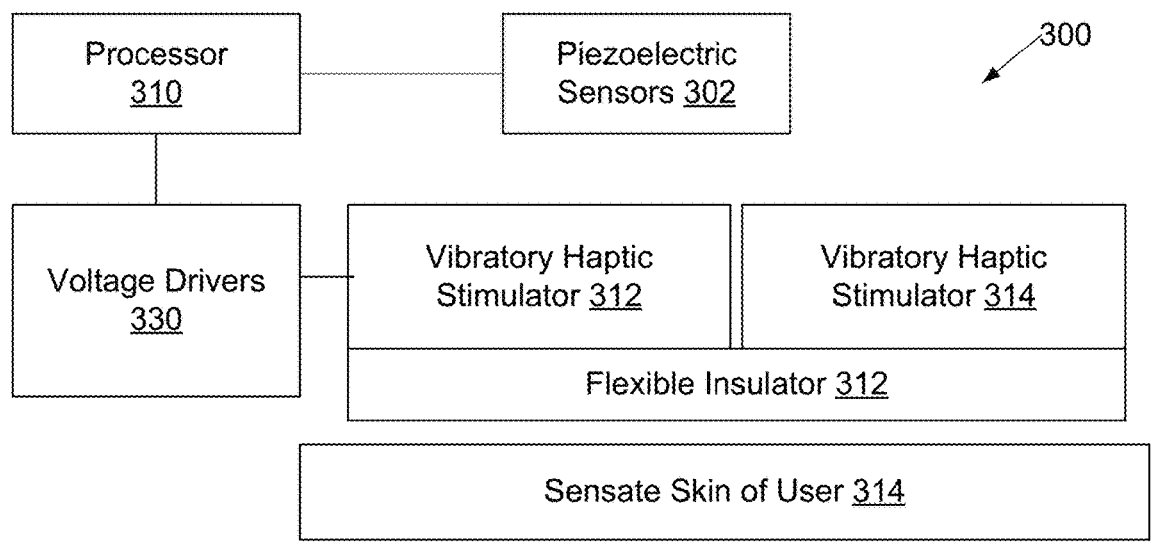
FIG. 6 is a functional block diagram of a system for providing touch sensation to a prosthetic using the polymeric piezoelectric devices herein described.
Figure 7:
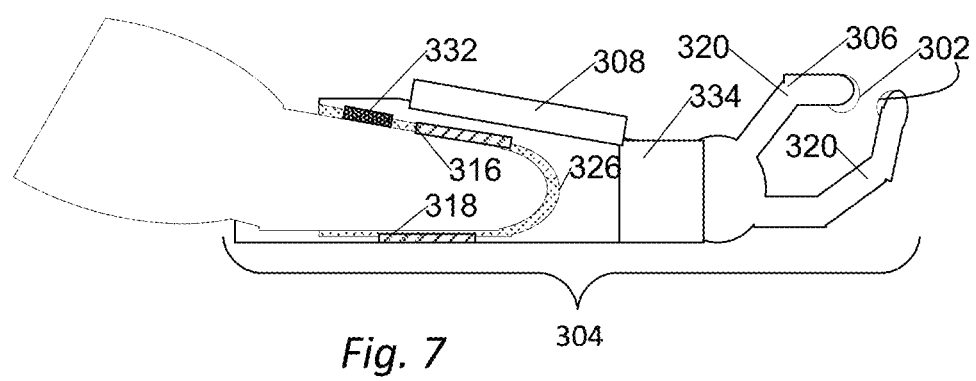
FIG. 7 is an outline sketch of a prosthetic embodying the system of FIG. 5.

A system 300 (FIG. 6) has piezoelectric pressure sensors 302, in a particular embodiment pressure sensors 302 are disposed within a prosthetic glove (not shown for simplicity) adapted to cover a terminal device of an upper-limb prosthetic 304 (FIG. 7), the pressure sensors being located over the contact surfaces of the terminal device. The terminal device may, but need not, have form of an artificial hand—many prosthetic wearers prefer other forms of terminal devices for particular tasks. The pressure sensors 302 are electrically coupled to a processor 310 located in an electronics and battery module 308 of the prosthetic by wires (not shown). The processor 310 is configured by firmware in a memory (not shown) to read the pressure sensors 302 and determine an appropriate level of vibration for each of several vibratory haptic stimulators 312, 314 piezoelectric polymer structures, which be the piezoelectric structures and devices described with reference to FIGS. 1-5. In a particular embodiment, haptic stimulators 312 may be located in a first array 316 adapted to represent multiple piezoelectric sensors 302 located over a contact surface of a first portion 320 of terminal device 306 and in a second array 318 adapted to represent multiple piezoelectric sensors 302 located over a contact surface of a second portion 322 of terminal device 306. In an embodiment, arrays 316 and 318 are located in different portions of a prosthetic liner 326 of prosthetic 304.

Signals from processor 310 are boosted to the high voltages necessary to drive the haptic stimulators 312, 314 by voltage drivers 330, also located within electronics and battery module 308. In embodiments, liner 326 is also equipped with a myoelectric sensor 332 coupled to a myoelectric-controlled motor driver (not shown) in electronics and battery module 308, the motor driver coupled to drive a motor 334 configured to operate terminal device 306.

Figure 20:
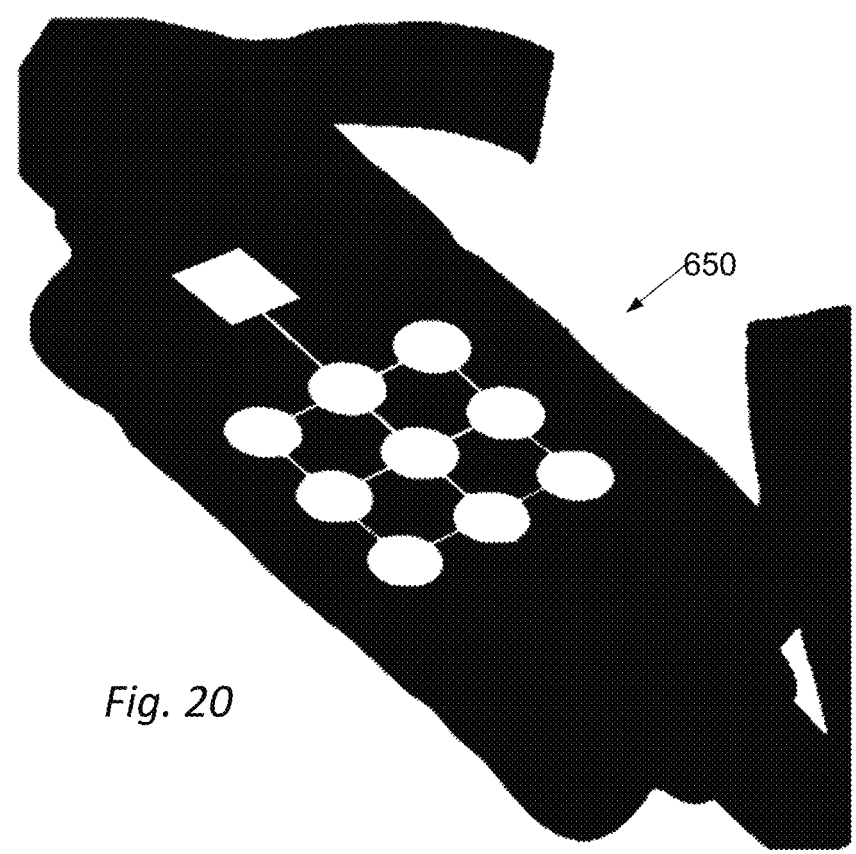
FIG. 20 illustrates a back pad having a haptic stimulator array.

In alternative embodiments, the haptic stimulators 312, 314, 600 may be located in a back pad 650 (FIG. 20), such a back pad may be particularly appropriate for use with a synthetic vision system for the blind.

Kirigami PVDF Devices

By using techniques from kirigami (the art of folding and cutting paper), we can selectively remove unnecessary parts of the film and make cuts to focus displacement in certain regions and to permit greater displacements than available with an intact, uncut, film.

Test devices were formed of PVDF film with metallic electrode patterns of gold sputtered onto top and bottom surfaces of the film using masks. This pattern determines which parts of the device contribute both electrically and mechanically to displacement, and which parts contribute only mechanically. A late step of manufacture is the kirigami cut, in which certain pieces of the film are excised to improve the overall device motion. We considered three kirigami-cut embodiments, spiral-cut, center-cut, and peripheral-cut.

Spiral Cuts

Figure 9:
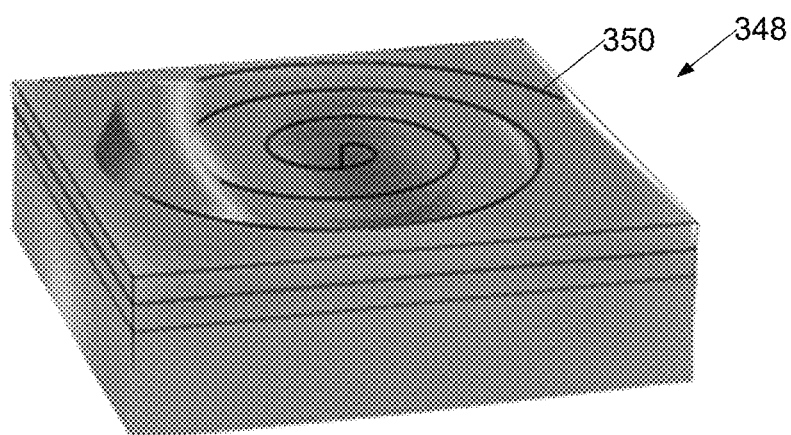
FIG. 9 is a perspective view illustrating an embodiment having a spiral Kirigami cut permitting additional excursion in vibration magnitude.
Figure 10:
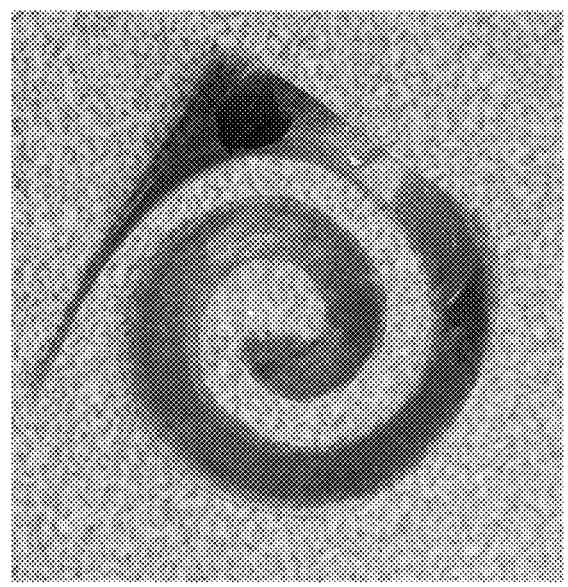
FIG. 10 is a top view of a fabricated prototype embodiment having a spiral Kirigami cut similar to that illustrated in FIG. 8.

An embodiment 348 (FIG. 9) has a spiral kirigami cut 350 permitting additional excursion in vibration magnitude beyond that obtained with uncut haptic stimulators. A spiral-cut piezoelectric structure has been fabricated and tested; see the photo in FIG. 10. The number of turns and width of the spiral cut significantly affect the resonant frequencies of the device, permitting adjustment of a design for a particular resonant frequency.

Center (Diagonal) Cuts

Figure 8:
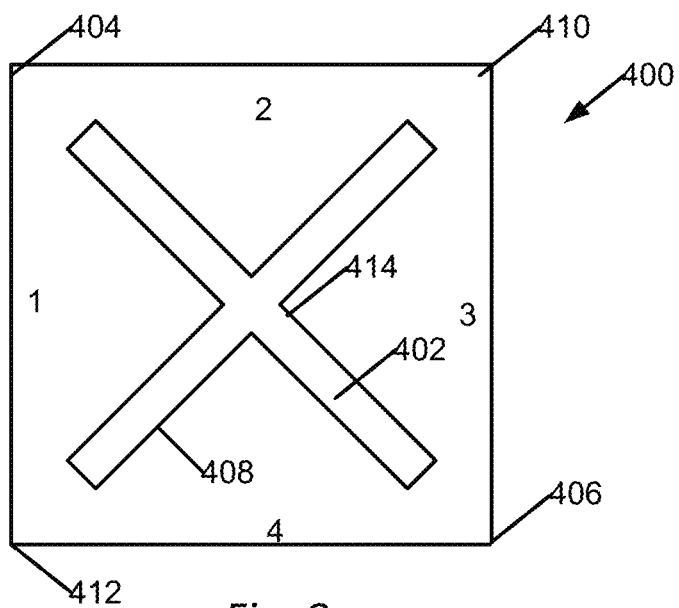
FIG. 8 is a top plan view of an embodiment having center cuts.

In a center-cut or diagonal-cut embodiment 400 (FIG. 8) the multilayer piezoelectric sheet with top and bottom electrodes is formed as a rectangle having all four perimeter edges attached to the substrate, the polymer layer has a first slit 402 positioned along a line defined by an intersection 404 of the first and second edges to an intersection 406 of the third and fourth edges, and a second slit 408 positioned along a line defined by an intersection 410 of the second and third edges to an intersection 412 of the first and fourth edges, the first and second slit intersecting near a center of the rectangle.

The center-cut embodiment permits the four points, such as point 414, to flex more freely than an uncut embodiment because the points can separate freely from each other as they lift toward their highest position. The result is increased vibration magnitude over an uncut embodiment while retaining more of the vibration force than typical with a spiral-cut embodiment.

Peripheral Cuts

Figure 11:
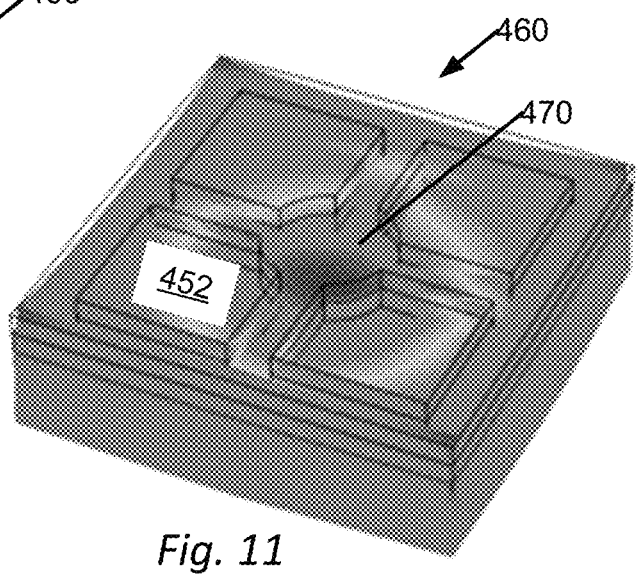
FIG. 11 is a perspective view illustrating an embodiment having peripheral cuts permitting additional excursion in vibration magnitude.
Figure 12:
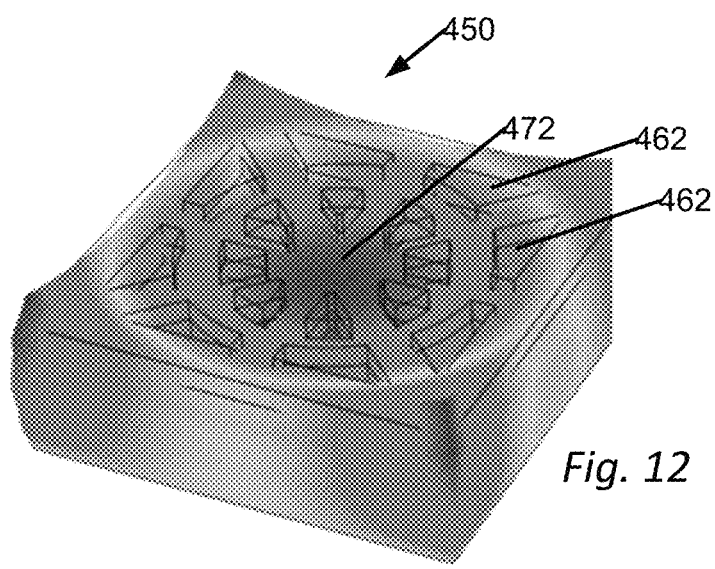
FIG. 12 is a perspective view illustrating another embodiment having peripheral cuts permitting additional excursion in vibration magnitude.

In another embodiment 450, 460 (FIGS. 11 and 12), in order to effectively reduce stiffness of the multilayer sheet and increase vibrational magnitude, without serious reduction in vibratory force, the device center is left without cuts, but multiple holes or cuts 452, 462 are positioned around a periphery of the sheet between device center 470, 472 and device edges.

Frequency Range

Embodiments of haptic stimulators as herein described have resonances, and may therefore be efficiently operated at, low frequencies below 200 hertz. In particular embodiments, the devices are efficient when operated in the frequency ranges from 5 to 200, from 60 to 200, from 20 to 84, or from 80-125 hertz.

Cantilevered Embodiment

Figure 13:
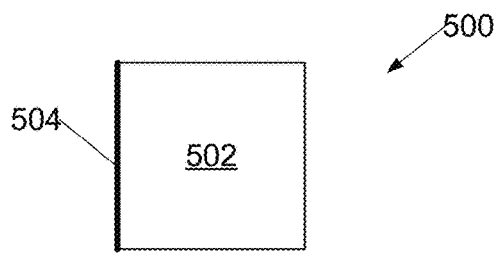
FIG. 13 is a top plan view of a rectangular embodiment supported on only one side of the rectangle.
Figure 14:
FIG. 14 is a lateral view of the embodiment of FIG. 13 illustrating significant displacement of the multilayer sheet because three sides are unsupported.

In an embodiment 500 (FIG. 13) the multilayer sheet is, unlike all previously described embodiments, supported only on one side 504 of the rectangular space allocated to each piezoelectric haptic stimulator. With the remaining three sides floating, the entire rectangle can flex, as seen in FIG. 14. It is believed that this embodiment could provide 600 mN of force and a millimeter of displacement with a one-centimeter square haptic actuator.

Electroactive Perimeter Frame

Figure 17:
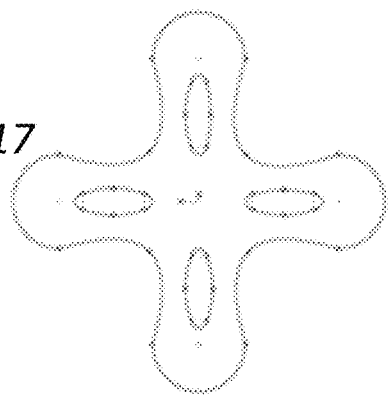
FIG. 15-17 illustrate several forms of stiff plating for electroactive polymer (EAP) devices.
Figure 16:
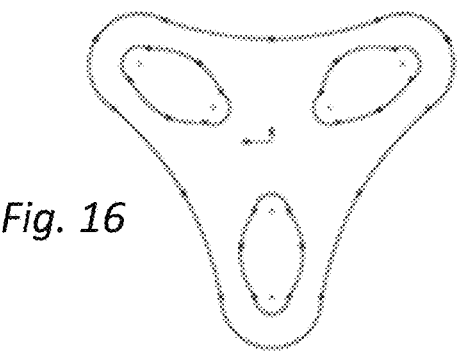
Figure 15:
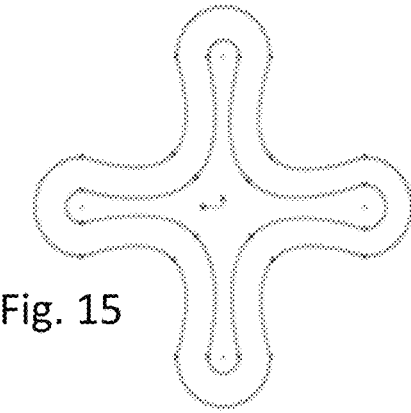
Figure 18:
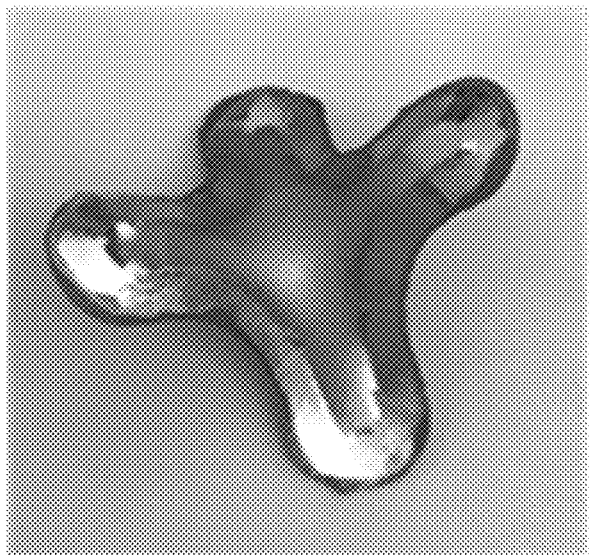
FIG. 18 illustrates curling of an EAP device of claim 15.

We experimented with using kirigami patterning (FIG. 15-17) to create stiff plating for electroactive polymer (EAP) devices. EAPs contract vertically and expand horizontally under application of high voltage. By fixing prestretched EAP films onto these kirigami backings, the devices could be induced to curl into specific shapes, as shown in FIG. 18, due to strain mismatch. When the EAP films were actuated, they would unfurl to a flatter state, dictated by the shape and size of the backing. The more material is removed from the backing, the higher the displacement and lower the force of the resulting device.

The soft material of electroactive polymers (EAPs), which deforms in response to application of an electrical stimulus, the forces induced by the EAPs may be used to trigger the snap-through of bistable structures. Preliminary results are applicable to both multi-stable structures. FIG. 15-18 give a few designs on EAP based actuators.

Electrostatic Haptic Stimulator

An electrostatic haptic stimulator 600 (FIG. 19) has a first electrode 602, a second electrode 604 formed of an electrically conductive layer disposed on a pre-deformed, domed, insulating sheet 606, with the second electrode configured parallel to and with an air gap from the first electrode. There is an insulating sheet 608 between the second electrode and the first electrode to prevent their shorting together. The stimulator 600 is driven by a high voltage source coupled through lead wires 610, 612, the lead wires contacting the electrodes. The top insulating sheet 604 is drawn downward by electrostatic forces when high voltage is present between the electrodes, and will therefore vibrate when driven by an AC voltage. The top insulating sheet 604 may directly contact sensate skin or may transfer vibration through a soft, overlying, insulator such as a glove, sock, or liner.

Figure 19:
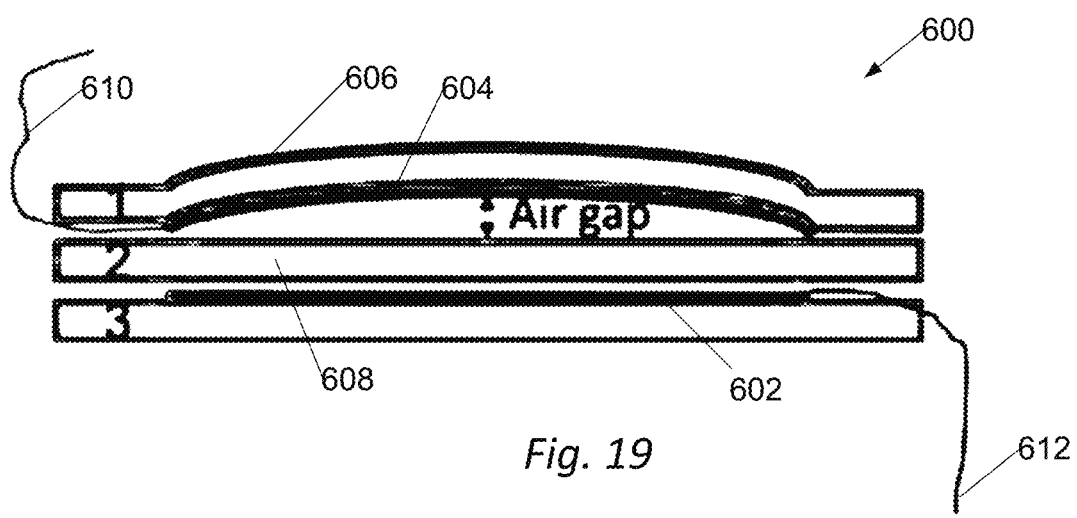
FIG. 19 is a cross sectional diagram of an electrostatic haptic stimulator.

A prototype of the electrostatic haptic stimulator of FIG. 19 has been observed to provide ten mN of force when driven with 800 volts at 10 hertz, with approximately 0.4 mm of vibrational magnitude—sufficient to be felt and to serve as a haptic stimulator.

By charging different parts of the upper or second electrode, this air gap can be localized to a specific portion of the device, and can be further moved controllably around the device by precisely switching the charging areas. Finally, when a load is placed on top of the device, the motion of the gap will transform into shear force. This technology can be seamlessly integrated into a wearable device to generate a feeling of shear motion on human skin.

In a particular embodiment, the top insulating sheet is configured to be bistable, so it retracts and pops outwards with distinct sharp motions.

Figure 4:
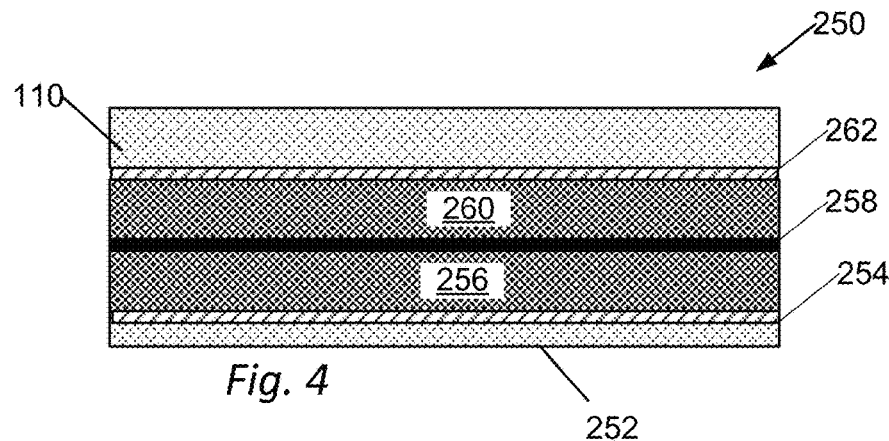
FIG. 4 is a cross section of a bimorph PVDF structure with top, center, and bottom electrodes and upper and lower PVDF layer.

In yet another embodiment, an electrostatic device of FIG. 19 is combined with a PVDF-TrFE layer device like that of FIG. 4, can be designed for both sensing and actuation, owing to the fact that PVDF-TrFE films can act as excellent pressure sensors. Specifically, a thin layer of piezoelectric PVDF can be placed underneath an air electrostatic gap device. When the device is compressed, the PVDF-TrFE will generate a voltage which can be extracted and correspond to a certain sensing level. This allows the device to act both as an actuator and a sensor with minimal increase in thickness or complexity.

In this invention, the air gap device using electrostatic mechanism can act as a force generator, and the sensing function is realized by utilizing the piezoelectric material. The array of air gap devices can increase the sensation level on human skin with simple designed structure by driving both the piezoelectric and electrostatic actuators.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An apparatus configured to stimulate sensate skin, the apparatus comprising:
   a multilayer sheet comprising a polymer layer adapted to mechanically deform upon application of a voltage to the polymer,
   the multilayer sheet secured to a substrate,
   the polymer being piezoelectric polyvinylidene fluoride;
   a first and a second electrode disposed upon the polymer layer, and
   a source of electrical stimulation coupled to drive the first and second electrode with an alternating current signal to vibrate the polymer layer;
   wherein the first and second electrodes are disposed on a first side of the polymer layer, the first and second electrodes being interdigitated;
   the multilayer sheet having a first edge attached to the substrate and a second edge free of the substrate, the second edge free of the substrate being adapted to stimulate the sensate skin.

2. The apparatus of claim 1 wherein the first and second electrodes are configured in a circular pattern of between two and three centimeters diameter.

3. The apparatus of claim 1 wherein the alternating current signal has a frequency corresponding to a vibrational resonance of the multilayer sheet.

4. The apparatus of claim 3 wherein the frequency is between 60 and 200 hertz.

5. A method of providing haptic stimulation to sensate skin comprising:
   coupling an alternating current signal generator to drive a first and second electrode of a multilayer sheet, the first and second electrode disposed upon a polymer layer comprising polyvinylidene fluoride, the polymer layer, first electrode and second electrode comprising a multilayer sheet; and
   vibrating the polymer layer by enabling the alternating current signal generator; and coupling vibrations of the polymer layer to the sensate skin;

wherein the first and second electrodes are disposed on a same first side of the polymer layer, the first and second electrodes being interdigitated, the multilayer sheet being configured with a first edge attached to a substrate and a second edge being free of the substrate and configured to stimulate the sensate skin.

6. The method of claim 5 wherein the first and second electrode are configured in a circular pattern of between two and three centimeters diameter.

7. The method of claim 5 wherein the alternating current signal generator has a frequency corresponding to a vibrational resonance of the multilayer sheet.

8. The method of claim 7 wherein the frequency is between 60 and 200 hertz.

* * * * *